United States Patent
Tyurina et al.

(10) Patent No.: US 10,144,001 B2
(45) Date of Patent: Dec. 4, 2018

(54) DEVICE, PROCESS, AND CATALYST INTENDED FOR DESULFURIZATION/ DEMERCAPTANIZATION/DEHYDRATION OF GASEOUS HYDROCARBONS

(71) Applicant: START-CATALYST LLC, Moscow (RU)

(72) Inventors: Liudmila Aleksandrovna Tyurina, Moscow (RU); Alexander Ivanovich Tyurin, Moscow (RU); Irina Gennadievna Tarkhanova, Moscow (RU); Alexey Aleksandrovich Tyurin, Moscow (RU)

(73) Assignee: START-CATALYST LLC, Moscow (RU)

( * ) Notice: Subject to any disclaimer, the term of this patent is extended or adjusted under 35 U.S.C. 154(b) by 0 days.

(21) Appl. No.: 15/539,882

(22) PCT Filed: Jul. 4, 2016

(86) PCT No.: PCT/RU2016/000416
§ 371 (c)(1),
(2) Date: Jun. 26, 2017

(87) PCT Pub. No.: WO2017/188847
PCT Pub. Date: Nov. 2, 2017

(65) Prior Publication Data
US 2018/0200699 A1    Jul. 19, 2018

(30) Foreign Application Priority Data

Apr. 25, 2016    (RU) ................. 2016116050

(51) Int. Cl.
*B01D 53/26* (2006.01)
*B01D 53/86* (2006.01)
(Continued)

(52) U.S. Cl.
CPC .......... *B01J 27/122* (2013.01); *B01D 53/263* (2013.01); *B01D 53/8603* (2013.01); *B01D 53/8612* (2013.01); *B01J 27/128* (2013.01); *B01J 27/32* (2013.01); *B01J 31/02* (2013.01); *B01J 31/16* (2013.01); *C07C 7/11* (2013.01); *C07C 7/1485* (2013.01); *B01D 2251/90* (2013.01); *B01D 2252/2023* (2013.01); *B01D 2255/20761* (2013.01); *B01D 2256/245* (2013.01);
(Continued)

(58) Field of Classification Search
CPC ........ B01D 53/1462–53/1468; B01D 53/1481; B01D 53/8603–53/8618
See application file for complete search history.

(56) References Cited

U.S. PATENT DOCUMENTS

2003/0103884 A1* 6/2003 Lynn ................. B01D 53/1468
423/220

FOREIGN PATENT DOCUMENTS

RU    2398735 C1 *    9/2010    ............. C01B 17/05

* cited by examiner

*Primary Examiner* — Cabrena Holecek
(74) *Attorney, Agent, or Firm* — Nadya Reingand; Yan Hankin

(57) ABSTRACT

This application is in the field of technologies for desulfurization and demercaptanization of raw gaseous hydrocarbons (including natural gas, tail gas, technological gas, etc, including gaseous media). It can be used for simultaneous dehydration and desulfurization/demercaptanization of any kind of raw gaseous hydrocarbons.

5 Claims, 2 Drawing Sheets

(51) Int. Cl.
*B01J 27/122* (2006.01)
*C07C 7/11* (2006.01)
*C07C 7/148* (2006.01)
*B01J 27/128* (2006.01)
*B01J 31/02* (2006.01)
*B01J 31/16* (2006.01)
*B01J 27/32* (2006.01)
*B01J 27/13* (2006.01)

(52) U.S. Cl.
CPC .. *B01D 2257/304* (2013.01); *B01D 2257/306* (2013.01); *B01J 27/13* (2013.01)

DEVICE, PROCESS, AND CATALYST INTENDED FOR DESULFURIZATION/DEMERCAPTANIZATION/DEHYDRATION OF GASEOUS HYDROCARBONS

CROSS-REFERENCE TO RELATED APPLICATIONS

The present application is a National stage application from the PCT application PCT/RU2016/000416 filed on Jul. 7, 2016 which claims priority to Russian application RU2016116050 filed on Apr. 25, 2016.

FIELD OF INVENTION

This application is in the field of technologies for desulfurization and demercaptanization of raw gaseous hydrocarbons (including natural gas, tail gas, technological gas, etc, including gaseous media). It can be used for simultaneous dehydration and desulfurization/demercaptanization of any kind of raw gaseous hydrocarbons.

BACKGROUND

A prior art (U.S. Pat. No. 4,622,212, issued on Nov. 11, 1986) describes a process of liquid-state oxidation of hydrogen sulfide to sulfur by means of chelating complexes of iron (Lo-Cat process). In the Lo-Cat process, a catalytic reactor for conversion of hydrogen sulfide into sulfur is used, and a device to regenerate the catalyst solution.

The said process features insufficient degree of desulfurization and incapability of demercaptanization and dehydration that must be admitted as its drawbacks.

A prior art (U.S. Pat. No. 8,735,316, issued on May 27, 2014) describes a process of catalytic demercaptanization by converting mercaptans to disulfides. As a catalyst, the complex CuCl with monoethanol amine (MEA), acetonitrile, or with a monobasic alcohol is used. The process flows in presence of air oxygen, at a temperature of 22-140° C. The residual amount of mercaptan sulfur can be reduced to 20 ppm.

The said process is capable of purifying only liquid media, and no data is provided concerning its capability of hydrogen sulfide removal and/or water removal, that must be admitted as the drawbacks.

A prior art (RU patent No. 2385180 issued on Mar. 27, 2010) describes a Claus-process of conversion of hydrogen sulfide to sulfur The said art features primary amine treatment of the gas to be purified, multiple stages of the process and insufficient conversion of hydrogen sulfide to sulfur, necessity of tail gas treatment, sophisticated technological equipment, and incapability of demercaptanization and dehydration, all these items must be admitted as the drawbacks.

A prior art (U.S. Pat. No. 5,286,697, issued on Feb. 15, 1994) also describes an improved Claus process.

The said art is also incapable of demercaptanization and dehydration, and it is less efficient in hydrogen sulfide conversion.

A prior art (RU patent No. 2,405,738, issued Apr. on 27, 2010) describes a means of sulfur recovery from industrial gases by means of a catalyst that contains on dehydroxylated silica gel (97.65% by mass) impregnated with ferric phosphate (III) (2.35%), that provides sulfur formation from hydrogen sulfide that is present in gaseous hydrocarbons.

The said art features insufficient conversion of hydrogen sulfide, and catalyst production complexity, incapability of gas dehydration, that must be admitted as drawbacks.

A prior art (RU patent No. 2,398,735, issued on Sep. 10, 2010) describes a means of gas desulfurization by oxidating hydrogen sulfide to elemental sulfur in liquid state in presence of a catalyst, which contains a compound of a transition metal and an organic complexing agent. To oxidate hydrogen sulfide, it is proposed to use air oxygen as oxidizer; as a compound of transition metal, cupric halogenide is used, where the amount of copper in the solution is 0.015 to 0.1% by weight, and where as an organic complexing agents, one of the following is used: dimethylformamide, pyrrolidone, methylpyrrolidone, pyridine, or quinolone; the process flows in a solvent that is taken as one of the following: monobasic alcohol, polybasic alcohol, water, or their mixtures, kerosene, isooctane, gas condensate at temperature of 20-40° C.

The drawbacks of the said process are its capability of gas desulfurization only, incapability of gas dehydration.

The closest technical solution to one described in the current claim can be considered the prior art (RU patent 2,127,146, issued on Mar. 10, 1999) that describes a process of gaseous hydrocarbon purification to $H_2S$ level below 4 ppm vol. and dehydration with dew point temperature in between 0° C. and −18° C. The said closest technical solution provides desulfurization and dehydration of the gas by applying a solution of "amine-glycol". The said process does not provide conversion of hydrogen sulfide into sulfur. Hydrogen sulfide extracted from the gas undergoes afterburning with generation of sulfur dioxide.

The drawbacks of the said process are related to hydrogen sulfide conversion to sulfur dioxide, that requires disposal, and incapability of demercaptanization.

SUMMARY

Current invention claim is free from the drawbacks of the prior art described above, in that it is capable of simultaneous gas dehydration and demercaptanization, where mercaptan sulfur recovery rate is over 99%, with no atmospheric emissions or any waste that requires disposal.

The technical problem solved by current invention is in developing a technical solution that provides simultaneous dehydration, desulfurization and demercaptanization while SH recovery rate is above 99.999%.

The technical result achieved in realization of proposed solution is a single-stage desulfurization and demercaptanization of gaseous hydrocarbons simultaneously with their dehydration while providing residual amount of —SH down to 0.001 ppm and producing no waste.

To achieve the said technical result, it is proposed to use the developed device for dehydration, desulfurization and demercaptanization of gaseous hydrocarbons. The proposed device for dehydration, desulfurization and demercaptanization of gaseous hydrocarbons is based on a device for absorptive gas dehydration where working temperature and pressure of the gas, and the composition of the absorbent are determined by requirements to gas dehydration. The proposed device features a reactor for desulfurization/demercaptanization/dehydration loaded with solution of a catalyst for conversion of hydrogen sulfide and mercaptans into sulfur and disulfides, respectively, dissolved in an absorbent. The proposed devices also features a unit for absorbent regeneration and sulfur separation.

While the gas is passed through absorbent solution of the catalyst the hydrogen sulfide and the mercaptans convert to sulfur and disulfides, respectively, in accordance with reaction formula:

$$H_2S+2RSH+O_2=S+RSSR+2H_2O \qquad (1)$$

The disulfides formed in reaction (1) remain in the reactor, and they do not affect the main process in any way. The water is absorbed by the absorbent solution, and it is withdrawn from the reactor together with fine sulfur dispersion. The purified and dehydrated gas is given out to the end user from the reactor outlet. The absorbent solution together with fine sulfur dispersion is passed over for regeneration and sulfur separation.

The device provides for a unit for sulfur pulp withdrawal from the reactor to the unit for absorbent regeneration and sulfur separation. In addition, the said device includes at least a means of supplying the gaseous hydrocarbons to be purified and the oxygen-containing gas into the reactor, a means of withdrawing the purified gas from the reactor, and the unit for absorbent regeneration and sulfur separation includes a means of absorbent regeneration and a means of sulfur removal from the unit, where the reactor design and catalyst composition provide conversion of at least 99.99% of hydrogen sulfide and mercaptans into sulfur and disulfides, respectively, with simultaneous water absorption by the absorbent in order to provide the required level of gas dehydration, and where the unit for absorbent regeneration provides for removing water from it with later absorbent recycling into desulfurization/demercaptanization/dehydration reactor.

In the preferred embodiment the means of supplying the gaseous hydrocarbons to be purified and the oxygen-containing gas additionally include a means of mixing the gaseous hydrocarbons to be purified with the oxygen-containing gas and homogenization of the resulting gas mixture, and the desulfurization/demercaptanization/dehydration reactor includes a means for distributing the supplied gas mixture in the reactor volume.

In some embodiments, the desulfurization/demercaptanization/dehydration reactor may additionally include filling plates.

In some embodiments, the device may additionally include a means of metered supply of the catalyst into desulfurization/demercaptanization/dehydration reactor, or into the unit for absorbent regeneration and sulfur separation, or into any other part of the device.

As a catalyst that provides the said technical result achievement, the device may use mixed-ligand complexes based on ferric and/or cupric halogenides. The any other catalyst composition may be used that provide achievement of the said technical result The unit for absorbent regeneration and sulfur separation typically includes at least an inlet nozzle to inlet the catalyst solution for regeneration, an outlet nozzle to outlet the catalyst solution after regeneration, a nozzle to outlet the dissolved gas, a heater of the sulfur pulp in the absorbent, filling plates for absorbent dehydration, a water withdrawal nozzle to withdraw water that has been evaporated from the absorbent at its regeneration.

The means of sulfur withdrawal from the unit may be a pipe where liquid sulfur flows.

To achieve the said technical result it is proposed to use the developed process of dehydration/desulfurization/demercaptanization of gaseous hydrocarbons. In the said process, the gaseous hydrocarbons to be purified are mixed with an oxygen-containing gas, pressurized and passed through a reactor loaded with a catalyst for oxidizing hydrogen sulfide and mercaptans dissolved in an absorbent that provides dehydration of the gas, where the catalyst is mixed-ligand complexes of transition metals, the conversion rate of hydrogen sulfide and mercaptans into sulfur and disulfides is at least 99.99%, and where the gas pressure determined by required moisture level in the purified medium.

Typically, the amount of oxygen is taken not less than 50% of total amount of hydrogen sulfide and mercaptan sulfur.

In some embodiments, the gas mixture supplied into the reactor is evenly distributed in the reactor volume.

Mostly due to catalyst loss, in the purification process, a metered supply of the catalyst is implemented.

Preferably, during the purification process, the fine sulfur dispersion is separated from the suspension by any known means, and the sulfur-free catalyst solution is recycled into the reactor.

Typically, as the absorbent for gas dehydration, glycols or glycol mixtures with organic compounds are used. At that, other absorbents may be used that provide achievement of the technical result said above.

Typically, in the said process a catalyst is used that is a 0.0001-100% solution in an organic solvent of mixed-ligand complexes based on ferric halogenide and/or cupric halogenide with addition of solvating agents.

Figure 1:
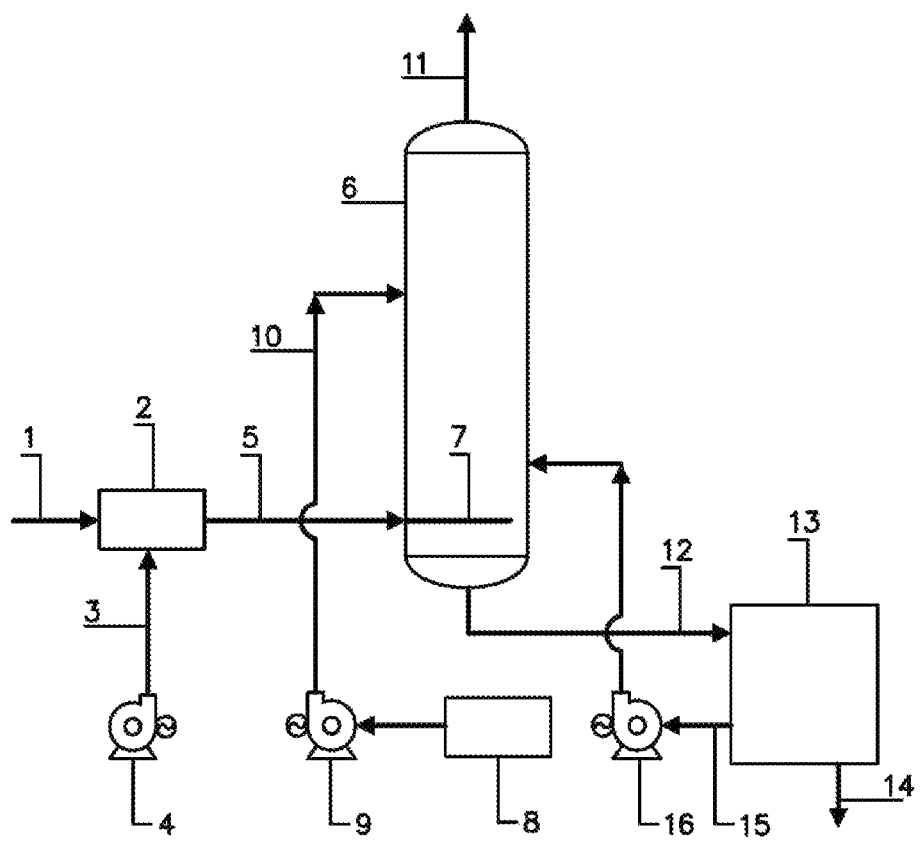
FIG. 1 shows the block diagram of the proposed device in the preferred embodiment where the following notations are used: pipeline 1 that supplies the raw gas to be purified, mixing unit 2 that mixes hydrocarbon gas to be purified with oxygen-containing gas, inlet pipe 3 that supplies oxygen-containing gas, agitator 4 of oxygen-containing gas discharge, pipe 5 that supplies mixture of hydrocarbon gas to be purified with oxygen-containing gas, desulfurization/demercaptanization/dehydration reactor 6, means 7 of distribution of mixture of hydrocarbon gas and oxygen-containing gas in the volume of reactor 6, tank 8 containing catalyst solution, agitator 9 of supply of catalyst solution from tank 8 into reactor 6, pipe 10 that supplies catalyst solution into reactor 6, pipe 11 that outlets purified gas, pipe 12 that outlets sulfur suspension into sulfur-separating unit 13, pipe 14 of sulfur outlet from sulfur-separating unit 13, pipe 15 that outlets catalyst solution from sulfur-separating unit 13 into reactor 6 after sulfur has been separated, agitator 16 of catalyst solution recycling from sulfur-separating unit 13 into reactor 6.
Figure 2:
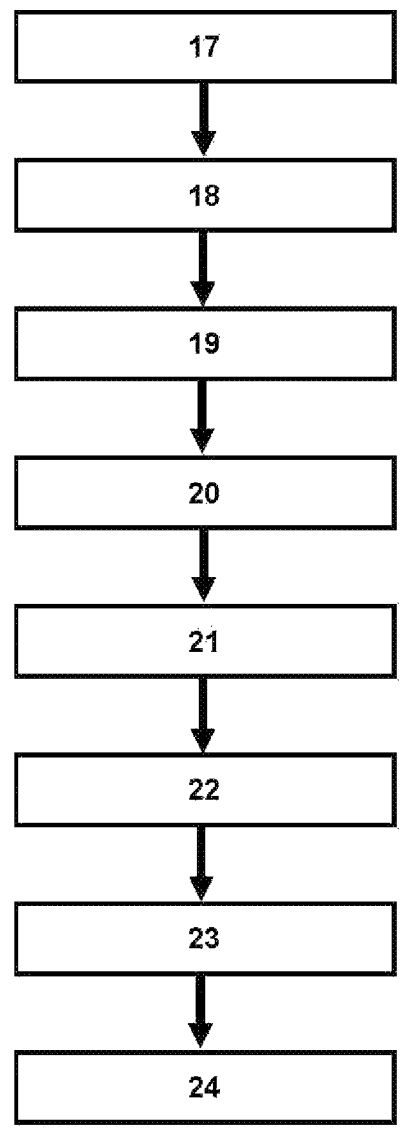

The general stages or the process realization are shown in FIG. 2, where the following notation is used: supplying raw hydrocarbon material mixed with oxygen-containing gas to the reactor—17, passing the raw material through the reactor loaded with a solution of a catalyst in an absorbent—18, output of pure gas from the reactor, where the conversion of hydrogen sulfide and mercaptans to sulfur and disulfides is 99.99%—19, usage of oxygen, not less than 50% of total amount of hydrogen sulfide and mercaptan sulfur—20, distribution of gas mixture evenly in the reactor volume—21, metered supply of the catalyst into the reactor—22, separation of sulfur from the suspension and recycling of catalyst solution into the reactor—23, maintaining of temperature in the device in range of 25-140° C.—24.

DETAILED DESCRIPTION OF THE PREFERRED EMBODIMENT

As an agitator of oxygen-containing gas discharge, an air compressor can be used, as an agitator of catalyst solution supply from the tank—a metering pump, and as an agitator of catalyst solution recycling from sulfur-separating unit—a regular pump can be used.

Below, the essence and advantages of the developed technical solution are discussed in examples of practical implementation.

Example 1

Synthesis of catalyst C1. Into a retort, at a room temperature, 50 ml of ethyl alcohol, 100 ml of octane, 0.2-10 g of $CuCl_2.2H_2O$ and 0.5-50 g of benzylamine are put. The contents of the retort are mixed until cupric chloride dissolves completely.

Example 2

Synthesis of catalyst C2. Into a retort, at a room temperature, 50 ml of ethyl alcohol, 100 ml of octane, 0.2-10 g of $CuCl_2.2H_2O$ and 0.5-50 g of cyclohexamine are put. The contents of the retort are mixed until cupric chloride dissolves completely.

Example 3

Synthesis of catalyst C3. Into a retort, at a room temperature, 50 ml of ethyl alcohol, 100 ml of octane, 0.2-10 g of $CuCl_2.2H_2O$ and 0.5-50 g of pyridine are put. The contents of the retort are mixed until cupric chloride dissolves completely.

Example 4

Synthesis of catalyst C4. Into a retort, at a room temperature, 50 ml of ethyl alcohol, 20 ml of water, 0.2-60 g of dimethylformamide (DMFA), and 0.2-10 g of $CuCl_2.2H_2O$ are put. The contents of the flask are mixed by means of a magnetic mixer until cupric chloride dissolves completely.

Example 5

Synthesis of catalyst C5. Into a retort, at a room temperature, 50 ml of alcohol, 0.2-60 g of mixture of amine (cyclohexamine, pyridine) with dimethylformamide (DMFA), 0.2-10 g of $CuCl_2.2H_2O$ are put. The contents of the flask are mixed until cupric chloride dissolves completely.

Examples 6-27

Gas purification using catalysts C1-C5. The reactor is loaded with glycol and one of the catalysts C1-C5 synthesized as in examples 1-5, respectively. The gas supplied into the reactor contains 1%-2.2% vol. of hydrogen sulfide, 0.05% of mercaptan sulfur and 0.5025%-1.125% vol. of oxygen. The gas pressure is 2.5-60 $kgf/cm^2$. The solution temperature is 25°-40° C. The output gas contains, according to potentiometric titration results, 0.001 ppm-70 ppm of hydrogen sulfide and mercaptan.

The rate of hydrogen sulfide removal is 99.6%-99.99999%, the rate of mercaptan removal is up to 99.998%. The rate of dehydration is determined by the gas pressure. The higher the gas pressure is, the lower amount of water remains in the output gas.

Experimental data on hydrogen sulfide, mercaptan and water contents after desulfurization/demercaptanization/dehydration of the gas using catalyst C1 is given in Table 1.

TABLE 1

| Example No | T, °C. | [$H_2S$] Input, % vol. | [$H_2S$] Output, ppm | [RSH] Input, % vol. | [RSH] Output, ppm | [$H_2O$], $g/m^3$ Input | [$H_2O$], $g/m^3$ Output |
|---|---|---|---|---|---|---|---|
| Gas pressure 6 $kgf/cm^2$ | | | | | | | |
| 6 | 25 | 1.5 | 40 | 0.05 | 50 | 3.584 | 0.424 |
| 7 | 40 | 1.5 | 60 | 0.05 | 60 | 8.284 | 0.939 |
| Gas pressure 25 $kgf/cm^2$ | | | | | | | |
| 8 | 25 | 1.5 | 45 | 0.05 | 60 | 1.069 | 0.135 |
| 9 | 40 | 1.5 | 45 | 0.05 | 60 | 2.425 | 0.291 |

Experimental data on hydrogen sulfide, mercaptan and water contents after desulfurization/demercaptanization/dehydration of the gas using catalyst C2 at temperature 25°-40° C. and under different conditions is given in Table 2.

TABLE 2

| Example No | T, °C. | [$H_2S$] Input, % vol. | [$H_2S$] Output, ppm | [RSH] Input, % vol. | [RSH] Output, ppm | [$H_2O$], $g/m^3$ Input | [$H_2O$], $g/m^3$ Output |
|---|---|---|---|---|---|---|---|
| Gas pressure 6 $kgf/cm^2$ | | | | | | | |
| 10 | 25 | 1.5 | 40 | 0.05 | 50 | 3.584 | 0.424 |
| 11 | 40 | 1.5 | 50 | 0.05 | 60 | 8.284 | 0.939 |
| Gas pressure 25 $kgf/cm^2$ | | | | | | | |
| 12 | 25 | 1.5 | 45 | 0.05 | 60 | 1.069 | 0.135 |
| 13 | 40 | 1.5 | 45 | 0.05 | 60 | 2.425 | 0.291 |

Experimental data given in Tables 1 and 2 show that the proposed device and process is capable of achieving the stated technical result even if the catalyst composition used is not optimal.

Experimental data on hydrogen sulfide, mercaptan and water contents after desulfurization/demercaptanization/dehydration of the gas using catalysts C1, C2, C3 at temperature 25°-40° C. and under different conditions is given in Table 3.

TABLE 3

| Example No | T, °C. | [$H_2S$] Input, % vol. | [$H_2S$] Output, ppm | [RSH] Input, % vol. | [RSH] Output, ppm | [$H_2O$], g/m3 Input | [$H_2O$], g/m3 Output |
|---|---|---|---|---|---|---|---|
| Gas pressure 6 $kgf/cm^2$ | | | | | | | |
| 14 | 25 | 1.5 | 50 | 0.05 | 60 | 3.584 | 0.424 |
| 15 | 40 | 1.5 | 60 | 0.05 | 70 | 8.284 | 0.939 |
| Gas pressure 25 $kgf/cm^2$ | | | | | | | |
| 16 | 25 | 1.5 | 45 | 0.05 | 60 | 1.069 | 0.135 |
| 17 | 40 | 1.5 | 45 | 0.05 | 60 | 2.425 | 0.291 |

Experimental data on hydrogen sulfide, mercaptan and water contents after desulfurization/demercaptanization/dehydration of the gas using catalyst C4 at temperature 25°-40° C. and under different pressure is given in Table 4.

TABLE 4

| Example No | T, °C | [H$_2$S] Input, % vol. | [H$_2$S] Output, ppm | [RSH] Input, % vol. | [RSH] Output, ppm | [H$_2$O], g/m3 Input | [H$_2$O], g/m3 Output |
|---|---|---|---|---|---|---|---|
| Gas pressure 6 kgf/cm$^2$ | | | | | | | |
| 18 | 25 | 1.5 | 40 | 0.05 | 50 | 3.584 | 0.424 |
| 19 | 40 | 1.5 | 45 | 0.05 | 50 | 8.284 | 0.939 |
| Gas pressure 25 kgf/cm$^2$ | | | | | | | |
| 20 | 25 | 1.5 | 40 | 0.05 | 60 | 1.069 | 0.135 |
| 21 | 40 | 1.5 | 40 | 0.05 | 60 | 2.425 | 0.291 |

Experimental data on hydrogen sulfide, mercaptan and water (g/m$^3$ and $T_{dew\ point}$, °C., water dew point temperature at P=3.92 MPa) contents after desulfurization/demercaptanization/dehydration of the gas using catalyst C5 at temperature 25°-40° C. and under different pressure is given in Table 5.

TABLE 5

| Example No | T, °C. | [H$_2$S] Input, % vol. | [H$_2$S] Output, ppm | [RSH] Input, % vol. | [RSH] Output, ppm | [H$_2$O] in output g/m$^3$ | $T_{dew\ point}$, °C. |
|---|---|---|---|---|---|---|---|
| Gas pressure 2.5 kgf/cm$^2$ | | | | | | | |
| 22 | 25 | 1.5 | 4 | 0.05 | 5 | 0.817 | 27 |
| Gas pressure 6 kgf/cm$^2$ | | | | | | | |
| 23 | 25 | 1.5 | 4 | 0.05 | 5 | 0.424 | 15.0 |
| 24 | 40 | 1.8 | 7 | 0.05 | 7 | 0.939 | 29.0 |
| Gas pressure 25 kgf/cm$^2$ | | | | | | | |
| 25 | 25 | 1.5 | 0.001 | 0.05 | 0.01 | 0.135 | −2.0 |
| 26 | 40 | 2.2 | 2 | 0.05 | 4 | 0.291 | 9.0 |
| Gas pressure 60 kgf/cm$^2$ | | | | | | | |
| 27 | 25 | 2.2 | 0.001 | 0.05 | 0.01 | 0.074 | −10.0 |

Hydrogen sulfide and mercaptan conversion in Examples 6-27 is given in Table 6.

TABLE 6

| Conversion, % | Example No | | | | | | | | | |
|---|---|---|---|---|---|---|---|---|---|---|
| | 6 | 7 | 8 | 9 | 22 | 23 | 24 | 25 | 26 | 27 |
| H$_2$S | 99.7 | 99.6 | 99.7 | 99.7 | 99.97 | 99.97 | 99.96 | 99.9999 | 99.991 | 99.9999 |
| RSH | 90.0 | 90.0 | 88.0 | 88.0 | 99.0 | 99.0 | 98.6 | 99.998 | 99.2 | 99.998 |

The examples provided show efficiency of the proposed device and process of hydrogen sulfide and mercaptans conversion. The amount of remaining water after dehydration therein is determined by process pressure and temperature, as is demonstrated in Tables 1-5. Under pressure 60 kgf/cm$^2$ the water content in the gas is reduced to 0.074 g/m$^3$, that corresponds to water dew point of −10° C.

Table 7 shows the results of gas purification by means of the proposed device and process with different concentration of catalyst C5. The conditions of the experiment are similar to those of experiments No. 6-27, temperature is 25° C.

TABLE 7

| [C5], % vol. | P, kgf/cm$^2$ | [H$_2$S] Input, % vol. | [H$_2$S] Output, ppm | [RSH] Input, % vol. | [RSH] Output, ppm | [H$_2$O] in output g/m$^3$ | $T_{dew\ point}$, °C. |
|---|---|---|---|---|---|---|---|
| 0.005 | 6 | 1 | 10 | 0.1 | 10 | 0.42 | 15 |
| 0.005 | 25 | 1 | 10 | 0.1 | 10 | 0.14 | −2 |
| 0.3 | 60 | 1 | 10 | 0.1 | 10 | 0.07 | −10 |

Table 8 shows results of purification and dehydration of gas having different hydrocarbon composition, with different contents of methane, $C_1$, ethane, $C_2$, and $C_{3+}$ by proposed device and process, using catalyst K 5. The conditions of experiments are similar to those of experiments No. 6-27.

TABLE 8

| Content, % vol. $C_1$ | $C_2$ | $C_{3+}$ | P, kgf/cm$^2$ | [H$_2$S] Input, % vol. | [H$_2$S] Output, ppm | [RSH] Input, % vol. | [RSH] Output, ppm | [H$_2$O], in output g/m$^3$ | $T_{dew\ point}$, °C. |
|---|---|---|---|---|---|---|---|---|---|
| 85 | 12 | 3 | 6 | 1 | 10 | 0.1 | 10 | 0.42 | 15 |
| 74 | 22 | 4 | 25 | 1 | 10 | 0.1 | 10 | 0.14 | −2 |
| 100 | | | 25 | 1 | 10 | 0.1 | 10 | 0.14 | −2 |
| 95 | 5 | | 60 | 1 | 4 | 0.1 | 5 | 0.07 | −10 |

The examples provided confirm achievement of the stated technical result, yet they do not show the limits of proposed technical solution.

It will be understood that the system and method may be embodied in other specific forms without departing from the spirit or central characteristics thereof. The present examples and embodiments, therefore, are to be considered in all respects as illustrative and not restrictive, and the system method is not to be limited to the details given herein.

What is claimed is:
1. A device for desulfurization, demercaptanization, and dehydration of gaseous hydrocarbons, comprising:
   a desulfurization/demercaptanization/dehydration reactor, said reactor being loaded with a catalyst for converting hydrogen sulfide and mercaptans into a sulfur and disulfides, respectively, in an absorbent solution, the catalyst comprising mixed ligand complexes based on ferric halogenides, cupric halogenides, or a mixture of ferric and cupric halogenides,
   a means for a sulfur pulp solution withdrawal from the reactor,
   a unit for sulfur separation and absorbent regeneration which receives the sulfur pulp solution, wherein an operating temperature, a gas pressure, and an absorbent composition are determined by gas dehydration requirements, wherein said device comprises at least a means for supplying into the reactor a gas to be purified and an oxygen-containing gas, a means for outletting a purified gas from the reactor, wherein the unit for sulfur separation and absorbent regeneration comprises a means for absorbent regeneration and a means for sulfur withdrawal from the unit for sulfur separation and absorbent regeneration, wherein the reactor and a composition of said catalyst are configured to provide a conversion of at least 99.99% of hydrogen sulfide and mercaptans into sulfur and disulfides, respectively, while at the same time achieving an absorption of water by an absorbent to a required degree of gas dehydration, wherein the means for absorbent regeneration provides for extraction of water from said absorbent with a later recycling of the absorbent into said desulfurization/demercaptanization/dehydration reactor.

2. The device of claim 1, wherein the means of supplying the gaseous hydrocarbons and oxygen-containing gas comprises a means for homogenization of a mixture of (1) a hydrocarbon gas to be purified and (2) an oxygen-containing gas.

3. The device of claim 1, wherein the reactor further comprises filling plates.

4. The device of claim 1, wherein the unit for sulfur separation and absorbent regeneration comprises at least a pipe for inletting a catalyst solution for regeneration, a pipe for outletting the catalyst solution after regeneration, a pipe for outletting a dissolved gas, a heater for heating a sulfur pulp solution in the absorbent, tip plates for absorbent dehydration, and a means for withdrawing water vapor from the absorbent solution.

5. The device of claim 1, wherein the means for sulfur withdrawal is a pipe through which liquid sulfur flows.

\* \* \* \* \*